United States Patent [19]

Ellenbogen et al.

[11] 3,966,978
[45] June 29, 1976

[54] 4-BIPHENYLACETIC ACID AS AN INHIBITOR OF PLATELET AGGREGATION

[75] Inventors: Leon Ellenbogen, New City, N.Y.; Constance Anne Kohler, Nutley, N.J.

[73] Assignee: American Cyanamid Company, Stamford, Conn.

[22] Filed: Apr. 25, 1975

[21] Appl. No.: 571,815

[52] U.S. Cl. .............................. 424/317
[51] Int. Cl.² ........................... A61K 31/19

[58] Field of Search ..................... 424/317

[56] References Cited
UNITED STATES PATENTS 3,784,704   1/1974   Cohen et al. ............ 424/317

Primary Examiner—Stanley J. Friedman
Attorney, Agent, or Firm—Jack W. Richards

[57] ABSTRACT

The use of 4-biphenylacetic acid in the amelioration of blood platelet aggregation.

4 Claims, No Drawings

4-BIPHENYLACETIC ACID AS AN INHIBITOR OF PLATELET AGGREGATION

BACKGROUND OF THE INVENTION

The compound 4-biphenylacetic acid is known and its preparation described in the literature, F. Blicke, et al., J. Am. Chem. Soc., 65, 1725 (1943). U.S. Pat. No. 3,784,704 also discloses the preparation of 4-biphenylacetic acid, and its use in producing long lasting amelioration of pain in warm-blooded animals. French Pat. No. 7,166M, patented Feb. 23, 1970, reports that 4-biphenylacetic acid possesses anti-inflammatory, antipyretic and analgesic activity.

Substituted 4-biphenylacetic acids are described, for example, in Irish Pat. No. 56/65, Belgian Pat. No. 664,187 (11/19/65), South African Pat. No. 65/4206 (3/10/66), French Pat. No. 2401M (4/13/64). These references describe a variety of uses for the substituted 4-biphenylacetic acids. Esters of biphenylacetic acid are described by F. Blicke, et al. (J. Am. Chem. Soc. 65, 1725 (1943) as antispasmodics although the base compound is not indicated as having any activity. G. Cavallini et al. (II Farmaco Ed. Scient. II, 167 (1956) describe a number of substituted biphenylacetic acids as having anti-cholesterolemic activity.) Other references such as British Patent 034,534 (1/14/71) and T. Y. Shen, Chim. Ther. 2 (3) 459 (1957) describe a number of substituted biphenylacetic acids as anti-inflammatory agents. To the best of our knowledge, however, no art is known which is concerned with the use of 4-biphenylacetic acid to treat thrombotic conditions such as those resulting from the aggregation of blood platelets.

The aggregation of blood platelets is an important mechanism in thrombosis and as the degree of aggregation increases the tendency of thrombus formation also increases. We have shown that 4-biphenylacetic acid inhibits the aggregation of the blood platelets of warm-blooded animals. 4-Biphenylacetic acid can be useful, as an antithrombotic agent, in the treatment of well known thrombotic conditions resulting from platelet aggregation. Such conditions include, for example, arterial thrombosis, pulmonary embolism, cerebrovascular disease, rheumatic heart disease, myocardial infarction, thrombophelebitis or thromboembolic conditions which may develop spontaneously following surgery, trauma or disease processes such as coronary occlusion and congestive heart failure. It can be useful in reducing transient ischemic attacks of the brain and possibly the heart. 4-Biphenylacetic acid may also be useful extrinsically in preventing the clotting of shed and/or stored blood and it is contemplated that its use as a platelet inhibitor extends both in vivo and in vitro platelet aggregation inhibition. It may be merely added to blood in vitro to prevent or inhibit platelet aggregation.

Numerous platelet aggregation inhibitors are known such as those disclosed in U.S. Pat. Nos. 3,692,836; 3,721,738; 3,735,005; 3,794,729; 3,795,582; 3,809,753; 3,859,288; and 3,862,319.

SUMMARY OF THE INVENTION

This invention contemplates the method of using 4-biphenylacetic acid and its pharmaceutically acceptable salts to inhibit blood platelet aggregation and thrombosis formation and compositions containing the acid and salts for such use.

In one aspect, this invention is concerned with a method of ameliorating thrombotic conditions in a warm-blooded animal caused or aggravated by blood platelet aggregation which comprises internally administering to said animal an effective amount of 4-biphenylacetic acid or a pharmaceutically acceptable salt thereof. In another aspect, this invention is concerned with a method of ameliorating thrombovascular diseases in a warm-blooded animal by the internal administration of the acid and salts disclosed herein. In still a further aspect, this invention is concerned with therapeutic compositions in unit dosage form having the ability to inhibit platelet aggregation in a warm-blooded animal when internally administered thereto containing 4-biphenylacetic acid or its pharmaceutically acceptable salts and a carrier. In another aspect, this invention is concerned with a method of treating blood to prevent platelet aggregation which comprises mixing with blood a platelet inhibiting amount of 4-biphenylacetic acid or its pharmaceutically acceptable salts.

DETAILED DESCRIPTION OF THE INVENTION

The following are illustrative examples of the invention.

EXAMPLE 1

Preparation of 4-Biphenylacetic acid

The compound can be prepared by the method of F. Blicke, et al., J.A.C.S., 65, 1725 (1943).

EXAMPLE 2

Preparation of Hard Shell Gelatin Capsules

| Ingredients | Amount |
| --- | --- |
| 4-Biphenylacetic acid | 10.0 g. |
| Magnesium stearate | 0.2 g. |
| Lactose | 12.0 g. |

The above ingredients are screened through a No. 40 mesh screen, transferred to a mixer and thoroughly mixed. The mixture is then placed in 100 conventional two piece hard shelled gelatin capsules. Each capsule contains a dose of 100 mg. of active component.

EXAMPLE 3

Preparation of Tablets

| Ingredients | Amount |
| --- | --- |
| 4-Biphenylacetic acid | 50 g. |
| Talc | 75 g. |
| Magnesium stearate | 2.5 g. |

The ingredients are mixed, screened and tableted to give 500 tablets each containing 100 mg. of active component.

EXAMPLE 4

Preparation of Oral Syrup

| Ingredients | Amount |
| --- | --- |
| 4-Biphenylacetic acid | 500 mg. |
| Sorbitol solution (70% N.F.) | 40 ml. |
| Sodium benzoate | 150 mg. |
| Saccharin | 10 mg. |
| Red dye (F.D. & C. No. 2) | 10 mg. |
| Cherry flavor | 50 mg. |

| -continued | |
|---|---|
| Ingredients | Amount |
| Distilled water qs ad | 100 ml. |

The sorbitol solution is added to 40 ml. of distilled water and the active ingredient is suspended therein. The saccharin, sodium benzoate, flavor and dye are added and dissolved in this solution. The volume is adjusted to 100 ml. with distilled water. Each ml. of syrup contains 5 mg. of drug.

EXAMPLE 5

Preparation of Soft Gelatin Capsules

| Ingredients | Amount |
|---|---|
| 4-Biphenylacetic acid | 50.0 g. |
| Peanut Oil | 112.5 g. |

Mix above ingredients to a thick slurry and fill into 1,000 soft gelatin capsules. Each capsule contains a dose of 50 mg. of drug.

EXAMPLE 6

Preparation of Parenteral Solution

In a solution of 700 ml. of propylene glycol and 200 ml. of water for injection is dissolved 20.0 g. of 4-biphenylacetic acid with stirring. After dissolution is complete, a solution of 5 g. of 2-aminoethanol in 20 ml. of water for injection is then added to the formulation. The pH of this solution is then adjusted to 5.5 with hydrochloric acid and the volume is made up to 1000 ml. with distilled water. The formulation is filtered through a 0.22 micron sterilizing filter, filled into 5.0 ml. ampoules each containing 2.0 ml. (representing 40 mg. of drug) and sealed under nitrogen.

The 4-biphenylacetic acid can be administered orally or parenterally to warm-blooded animals either alone or in the form of pharmaceutical preparations containing 4-biphenylacetic acid as the active or main active ingredient in order to achieve the desired effect. 4-Biphenylacetic acid may be used as the sole agent or it may be combined with other known platelet aggregation inhibitors or antithrombotic agents such as aspirin, or with still other drugs administered for a different purpose. Pharmaceutical preparations containing 4-biphenylacetic acid or its salts and conventional pharmaceutical carriers can be employed in unit dosage forms such as solids, for example, tablets, pills and capsules, or liquid solutions, suspensions or elixirs for oral administration, or liquid solution, suspensions, emulsions, and the like for parenteral use.

The quantity of 4-biphenylacetic acid administered can vary over a wide range to provide from about 0.5 mg./kg. to about 250 mg./kg. of body weight of animal per day. Unit doses of the compound can contain from about 1 mg. to about 250 mg. of the compound and may be administered once daily or in multiple or divided daily doses. The preferred range of dose is usually from 5 to 50 mg./kg./day. In terms of drug per dosage unit for internal administration, one or more at intervals of one or several times a day may vary from about 50 mg. to about 500 mg. of therapeutic component.

For oral use the 4-biphenylacetic acid can be administered orally to warm-blooded animals, either alone or in the form of conventional pharmaceutical dosage forms, e.g., tablets or capsules. For parenteral use, the acid or its salts can be dissolved in the appropriate solvent and prepared for injection according to methods known in the art.

Oral pharmaceutical preparations containing the compound of this invention and conventional pharmaceutical carriers can be employed in unit dosage forms such as tablets, capsules, liquids, suspensions, elixirs and the like for oral administration. Sustained release forms are also applicable. The pharmaceutical carriers of the present invention may be, for example, either a solid or a liquid. Exemplary of solid carriers are lactose, magnesium stearate, terra alba, sucrose, talc, stearic acid, gelatin, agar, pectin or acacia. Exemplary of liquid carriers are peanut oil, olive oil, sesame oil and water. Similarly, the carrier or diluent may include a time delay material such as glyceryl monostearate or glyceryl distearate alone or with a wax.

A wide variety of pharmaceutical forms can be employed. Thus, if a solid carrier is used, the preparation can be tableted, placed in a hard gelatin capsule or in the form of a troche or lozenge. The amount of solid carrier will vary widely but preferably will be from about 25 mg. to about 1 gm. If a liquid carrier is used, the preparation may be in the form of a soft gelatin capsule or a liquid suspension. For therapeutic administration the acid or appropriate salts thereof, may be incorporated with excipients and used in the form of dragees, elixirs, emulsions, suspensions, powders, syrups, etc.

4-Biphenylacetic acid was tested essentially according to the method of G. V. R. Born, Nature, No. 4832, pp. 927–929 (1962) and J. R. O'Brien, J. Clin. Path., 15, 446–452 (1962). Various concentrations of the compound were added in vitro to human platelet rich plasma. Collagen (final concentration 500 mcg./ml.) was added to induce platelet aggregation. Inhibition of platelet aggregation was determined by measuring the change in the optical density of the platelet rich plasma. The results of such a test appear in Table I. The degree of reduction in platelet aggregation by 4-biphenylacetic acid is expressed as the percent inhibition of maximum aggregation response to collagen in a control sample.

Table I

| Compound | Concentration mcg./ml. | Percent Inhibition |
|---|---|---|
| 4-Biphenylacetic acid | 250 | 40.7 |
| | 25 | 38.6 |

In a second test the in vivo activity of the compound was established. In this test the compound was administered orally to male rats at a concentration of 100 mg./kg. After one to two hours, the rats were bled and platelet rich plasma obtained. Collagen, at a concentration of 500 mcg./ml. was added to induce platelet aggregation and comparisons were made between control and treated samples. The percent inhibition of aggregation produced by the compound of this invention appears in Table II.

Table II

| Compound | Percent Inhibition |
| --- | --- |
| 4-Biphenylacetic acid | 12 |

In a third test the in vivo activity of 4-biphenylacetic acid was determined in mice. By in vivo measurement it was determined that this compound inhibits the respiratory depression associated with platelet aggregation and thrombosis induced by arachidonic acid.

Mice were treated orally by gastric lavage with 4-biphenylacetic acid in a starch suspension at a concentration of 100 mg./kg. Two hours later a challenge dose of arachidonic acid was given to the mice intravenously at a concentration of 50 mg./kg. The period of respiratory distress for each animal was recorded in seconds by observation. The results appear in Table III in comparison with controls who received only starch vehicle.

Table III

Effect of 4-Biphenylacetic Acid on Respiratory Depression Induced by Arachadonic Acid

| Animals | Controls (Time in Seconds) | Treated |
| --- | --- | --- |
| 1 | 635 | 100 |
| 2 | 535 | 420 |
| 3 | 560 | 200 |
| 4 | 550 | 30 |
| 5 | 435 | 150 |
| 6 | 795 | 170 |
| 7 | 470 | 80 |
| 8 | 390 | 195 |
| 9 | 180 | 125 |
| 10 | 570 | 35 |
| 11 | 450 | 170 |
| 12 | 360 | 120 |
| 13 | 200 | 25 |
| 14 | 240 | 20 |
| 15 |  | 60 |
| 16 |  | 50 |
| 17 |  | 90 |
| 18 |  | 75 |
| 19 |  | 70 |
| 20 |  | 189 |
| 21 |  | 60 |
| Average | 7.58 (minutes) | 1.93 (minutes) |

We claim:
1. A method of producing an inhibitory effect on blood platelet aggregation which comprises incorporating into the blood of a thrombotic warm-blooded animal an effective amount of 4-biphenylacetic acid or a pharmaceutically acceptable salt thereof.
2. A method of ameliorating thrombotic conditions in a warm-blooded animal associated with blood platelet aggregation, which comprises internally administering to said animal an effective amount of 4-biphenylacetic acid or a pharmaceutically acceptable salt thereof.
3. A method according to claim 2 wherein said administration is orally.
4. A method according to claim 3 wherein 4-biphenylacetic acid is administered to provide a daily dosage of from about 0.5 to about 250 mg./kg./day of body weight of said animal.

* * * * *